United States Patent [19]

Knowlton

[11] Patent Number: 5,301,692

[45] Date of Patent: Apr. 12, 1994

[54] METHOD FOR TOTAL, IMMEDIATE, POST-MASTECTOMY BREAST RECONSTRUCTION USING A LATISSIMUS DORSI MYOCUTANEOUS FLAP

[76] Inventor: Edward W. Knowlton, 25 Chestnut Pl., Danville, Calif. 94506

[21] Appl. No.: 979,493

[22] Filed: Nov. 16, 1992

[51] Int. Cl.$^5$ .................... A61B 19/00; A61F 2/12; A61F 2/54
[52] U.S. Cl. .................... 128/898; 128/897; 623/8; 623/66
[58] Field of Search .................... 128/897, 898; 623/66, 623/8, 11, 7

[56] References Cited

U.S. PATENT DOCUMENTS

| | | | |
|---|---|---|---|
| 4,372,293 | 2/1983 | Vijil-Rosales | 623/7 |
| 4,624,671 | 11/1986 | Kress | 128/898 X |
| 4,840,629 | 6/1989 | Bustos | 128/898 X |

Primary Examiner—Randall L. Green
Assistant Examiner—Dinh X. Nguyen
Attorney, Agent, or Firm—Timothy J. Lithgow

[57] ABSTRACT

A technique for immediate, total breast reconstruction is described that equally preserves the skin of both the mastectomy and remaining breast. The technique is most applicable to a mastectomy which is performed through a circumareolar incision. Replacement tissue for the excised nipple-areolar complex is provided by a latissimus dorsi flap having a cutaneous peg. The pectoralis major and latissimus dorsi flap serve to create a submuscular prosthetic compartment. The submuscular compartment, together with the volume of the latissimus dorsi flap, closely approximates the volume of the contralateral breast, and the normal contour of the breast skin envelope. Accordingly, insertion of a permanent implant instead of an expander is possible. The nipple-areolar reconstruction can also be completed at the initial operative stage.

31 Claims, 7 Drawing Sheets

METHOD FOR TOTAL, IMMEDIATE, POST-MASTECTOMY BREAST RECONSTRUCTION USING A LATISSIMUS DORSI MYOCUTANEOUS FLAP

FIELD OF THE INVENTION

The invention relates to a medical procedure, and more specifically to a surgical method that can provide an aesthetically pleasing breast reconstruction from a single-stage procedure.

BACKGROUND

Cancer of the female breast is a significant health matter worldwide. The current treatment of breast cancer includes surgery, chemotherapy and radiation therapy, as well as various combinations of these three modalities. Approximately one-half the women in the U.S. that are diagnosed with breast cancer will elect or will require a mastectomy. Thus, mastectomy procedures are commonly used for the treatment of breast cancers.

Mastectomies have been performed since the late 1800s, by a procedure commonly known as the Halstead radical mastectomy. During this procedure, the breast tissue and the pectoralis major muscle along with a variable amount of skin including the nipple-areolar complex is removed. Typically, an axillary lymph node dissection is performed concurrently with the mastectomy. This procedure leaves the patient with a Halstead radical mastectomy deformity which is disfiguring and is often emotionally traumatic. The deformity is especially disfiguring when skin grafting is required to close the defect.

The Halstead (radical mastectomy) procedure has been modified by preserving the pectoralis major muscle (a "modified radical mastectomy"), and by reducing the skin excision to allow for direct linear closure of the defect.

In the past, mastectomy closure techniques have included split thickness skin grafts attached directly to the rib cage, in the context of a Halstead radical mastectomy, or simple straight line closure of an elliptical skin excision. Closure of the skin defect could also involve the immediate incorporation of a cutaneous or myocutaneous flap to at least partially replace the resected tissue. Myocutaneous units are commonly used to cover defects, whether traumatic or post-resectional. A myocutaneous unit can be prepared as a combination of both skin and muscle, or as a muscle unit that subsequently can be skin grafted. A myocutaneous unit may be transferred as a free flap (a flap detached from its intrinsic blood supply), thereafter connecting the unit's axial blood supply to recipient vessels near the defect.

Latissimus dorsi or rectus abdominis myocutaneous flaps are the most frequently utilized myocutaneous flaps for mastectomy closure. Some common applications for latissimus dorsi flaps include coverage of defects in the head and neck area, especially defects created from major head and neck cancer resection. Other applications include coverage of chest wall defects other than mastectomy deformities. The latissimus dorsi may also be used as a reverse flap, based upon its lumbar perforators, to close congenital defects of the spine such as spina bifida or meningomyelocele.

Figure 1:
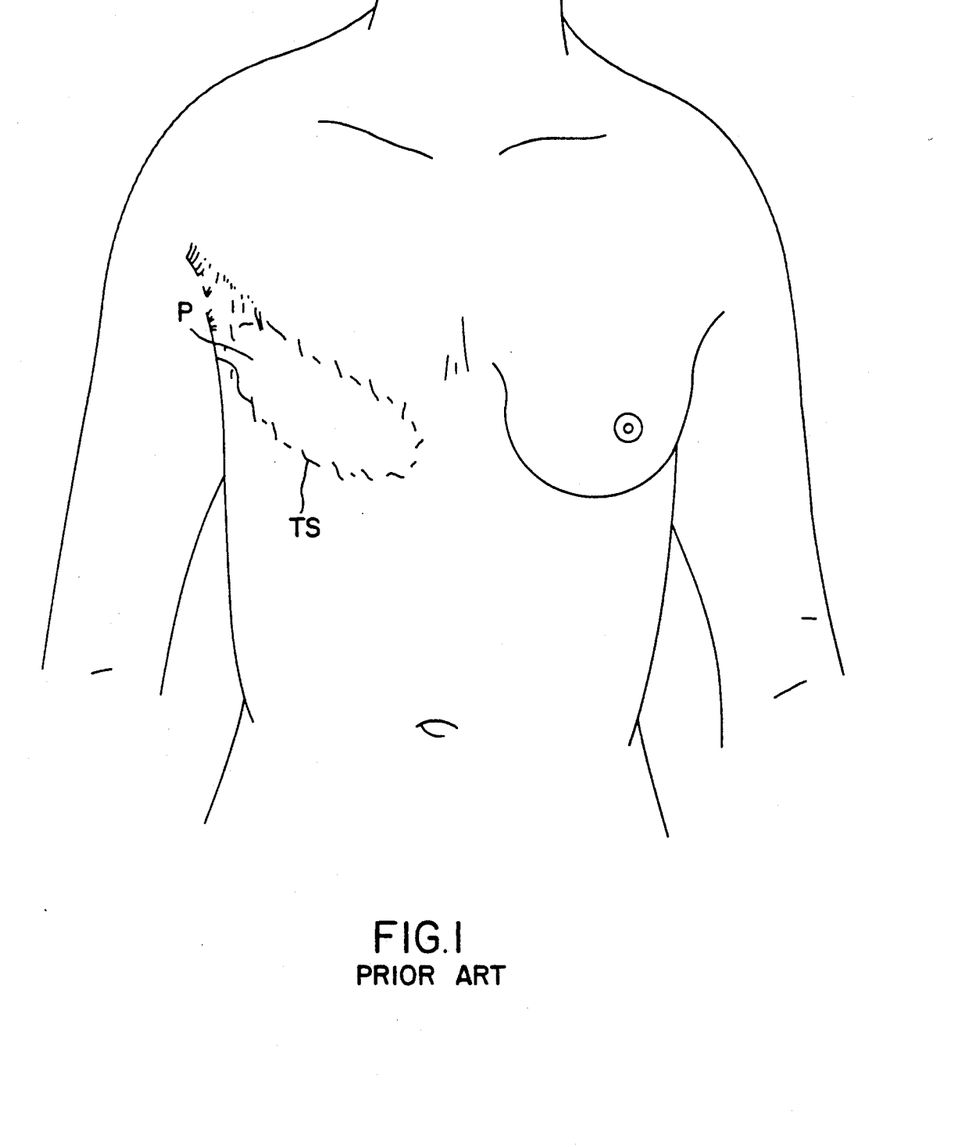
FIG. 1 illustrates a surgical result from a prior art latissimus dorsi reconstructive procedure following a radical mastectomy.

The latissimus dorsi myocutaneous flap procedure was first combined with the Halstead mastectomy by Dr. Tansini in Italy in 1906. (Maxwell: *Iginio Tansini and the Origin of the Latissimus Dorsi Musculocutaneous Flap, Plastic and Reconstructive Surgery* 65(5):686–692 (1980)) As illustrated in FIG. 1, a latissimus dorsi myocutaneous flap having a cutaneous paddle P, was used to close the mastectomy defect. This myocutaneous flap has an intrinsic axial blood supply that is critical to the transfer and survivability of the flap.

Prior to the development of the Tansini procedure, random cutaneous flaps had limited survivability due to the paucity of their blood supply. The Tansini procedure did not, however, result in breast reconstruction. The flap was used only to close the chest wall defect.

Mastectomy closure techniques serve only to close the excision site. Due to the adverse characteristics of a mastectomy deformity, either from a radical mastectomy or a modified radical mastectomy, many women opt for post-mastectomy breast reconstruction. Reconstruction can take place contemporaneously with the mastectomy, or at a later time.

To achieve breast reconstruction, it is common to use a submuscular breast expander or a permanent implant in conjunction with a mastectomy closure technique. A breast expander allows for, and generally requires, sequential addition of fluid which stretches the remaining breast tissue. Accordingly, expanders or implants are inserted beneath the mastectomy incision, and have been used as a method for either immediate or delayed breast reconstruction.

There are several disadvantages to postmastectomy use of former latissimus dorsi myocutaneous flaps for excision closure or for breast reconstruction. In either of these contexts, there is always a significant transverse scar across the chest. Transverse scarring Ts is illustrated, for example in FIG. 1. The donor site scar on the back is also substantial. When such procedures are used and a breast is then reconstructed, the disadvantages are exacerbated since there is a large elliptical paddle of skin across the breast. This skin paddle has different pigmentation than the adjacent breast skin. Furthermore, the large flap of skin does not adequately recreate the contour of the breast. The resulting breast was typically malformed and flat.

Previously, major resections of skin occurred during radical or modified radical mastectomy procedures. More recently, skin resection has been limited to the nipple-areolar complex, through a circumareolar or periareolar incision. Modified radical mastectomies with circumareolar incisions have been performed on patients who did not have pre-existing invasion of the surrounding breast skin. When the skin excision is limited to the region of the nipple-areolar complex, the skin envelope of the breast is preserved.

When a circumareolar mastectomy is performed via an excision of the nipple-areolar complex, a straight line closure with insertion of breast expander has been used. (Grossman et al.: *An Alternative Technique for Modified Radical Mastectomy with Immediate Reconstruction. Contemp. Surg.* 38(6):20–24, (1991)) When the mastectomy and reconstruction are completed a breast expander or permanent implant is inserted, and the incision is closed with a straight line closure. Consequently, the reconstructed breast is skin deficient in comparison to the contralateral breast. This tissue shortage frequently required a repositioning surgery, with resulting scarring, on the contralateral breast.

Heretofore, a latissimus dorsi flap procedure has not contemporaneously been combined with a circumareolar mastectomy. For example, the state of the art for immediate breast reconstruction was discussed at the most recent (1992) Annual Scientific Meeting of the American Society of Plastic and Reconstructive Surgeons, in Washington D.C. Notably, when discussing the use of latissimus dorsi flaps for immediate reconstruction, this procedure was not discussed in combination with a circumareolar mastectomy. Rather, the latissimus dorsi flap was described as a myocutaneous unit with a large elliptical paddle of skin extending well beyond the boundary of the nipple areolar complex. (Van Natta: *Use of the Latissimus Dorsi Myocutaneous Flag for Immediate Breast Reconstruction*, oral presentation and written abstract provided Sep. 22, 1992)

Although latissimus dorsi myocutaneous flaps have not been combined with a circumareolar mastectomy, trans-rectus abdominis muscle flaps (TRAM flaps) have been used in combination with a circumareolar mastectomy. TRAM flaps serve to close a mastectomy defect and to provide breast reconstruction. With the TRAM flap a circular skin island is designed and transferred to the mastectomy defect. However, this skin island does not result in a reconstructed breast having a nipple-areolar complex with the same projection as a normal breast. In a TRAM flap procedure, the subcutaneous tissue of the flap, rather than a breast implant, fills the void left by the removal of the breast tissue. The subcutaneous tissue is primarily adipose tissue. The transferred rectus abdominis muscle functions merely as a conduit of the vascular supply. Typically, the muscular component of the TRAM flap does not serve to create a structural component of the reconstructed breast, such as a submuscular prosthetic pocket. With TRAM flaps, there is no muscular sling to be used in creating a prosthetic compartment to achieve breast volume. Rather, the majority of the reconstructed breast volume is filled by adipose subcutaneous tissue of the TRAM myocutaneous unit.

There are several disadvantages with TRAM flaps. The flap loss rate is higher, because the circulation of the myocutaneous unit is less reliable with TRAM flaps than with latissimus dorsi flaps. In many cases, a nipple-areolar reconstruction with harvesting of the patient's own areola is not possible due to the paucity of TRAM flap blood supply.

The TRAM flap is placed on top of the pectoralis muscle. Thus, an inherent disadvantage of the TRAM flap procedure is that a chest wall cancer recurrence can be covered up by this flap, which could delay the diagnosis of chest wall cancer recurrence. Since subcutaneous adipose tissue provides the majority of the reconstructed breast volume, fat necrosis of this tissue is a significant complication with this procedure. When fat necrosis of the adipose tissue occurs, calcifications and connective tissue masses can result. These sequelae can further exacerbate the difficulty of diagnosing a chest wall cancer recurrence.

In infrequent situations, the TRAM flap has been used with a pre-muscular breast prosthesis. Such pre-muscular prostheses also exacerbate the difficulty of detecting any chest wall cancer recurrence.

The donor site scar is also a significant drawback to the TRAM procedure, since it is located on the lower abdomen and runs hip to hip. Patients may also be subject to abdominal wall weakness and hernia formation as one or two rectus muscles are transferred to the breast.

The TRAM flap can be performed only once. Breast reconstruction for any subsequent breast cancer would require the use of a different technique. Furthermore, use of a TRAM flap is severely limited if the woman has any abdominal scars or if the woman has an inadequate amount of subcutaneous tissue. These limitations are especially problematic when attempting to reconstruct a large breast. Due to the involved nature of TRAM flap surgery, the procedure is often excluded for patients who have risk factors such as smoking, diabetes, or pulmonary dysfunction.

A free gluteal flap may also be designed in a similar fashion to the TRAM flap. The gluteal flap would suffer the same disadvantages as the TRAM flap, as well as the disadvantages attendant to free flaps.

In general, there are several significant drawbacks with prior breast reconstruction procedures when used in combination with a standard modified radical mastectomy. Severe scarring is one of the most serious problems. Due to the substantial contour distortion produced by these techniques, a reliable method of immediate and total breast reconstruction could not be performed, since it was difficult to determine where the nipple-areolar complex should be placed in a one-stage procedure. Thus, such procedures necessitate a multiple stage breast reconstruction that must be carried out over several months. Each subsequent procedure carries additional surgical risks, such as infection, bleeding, and anesthetic complications. After the breast is reconstructed, the resulting breast has an artificial appearance due to the large amounts of skin resection. Frequently, repositioning of the contralateral breast is required due to loss of skin on the mastectomy side.

SUMMARY AND OBJECTS OF THE INVENTION

It is an object of the invention to provide a single-stage breast reconstruction technique that greatly limits the extent of the post-mastectomy deformity resulting from a circumareolar modified radical mastectomy. It is also an object of the invention to set forth a breast reconstruction procedure that can be performed bilaterally, and which is effective for any breast size. Accordingly, a modified radical mastectomy is performed through a circumareolar incision. The circumareolar mastectomy is contemporaneously combined with a latissimus dorsi flap breast reconstruction. A latissimus dorsi myocutaneous flap having a substantially circular peg of skin is then moved from the region of the back and brought into the region of the breast defect. The size of the peg on the latissimus dorsi flap corresponds to the size and shape of the excised nipple-areolar complex. A subpectoral pocket can then be created. The subpectoral pocket is expanded by attachment of the latissimus dorsi muscle flap along the inferior border of a pectoralis major muscle, thereby creating a larger submuscular pocket. This submuscular pocket is capable of corresponding to the topography of breast skin envelope preserved by the circumareolar mastectomy. If required, a permanent implant is introduced through the area of the excised nipple-areolar complex and placed into the submuscular pocket. The submuscular compartment is then closed. The incision is closed by attaching the margin of the peg to the margin of the incision. Lastly, a nipple-areolar reconstruction can be performed. The nipple-areolar complex can be formed from the skin peg of the latissimus dorsi flap. Furthermore, the areola can be harvested from the excised tissue. The harvested areola can be used as a graft for the reconstructed nipple-areolar complex, with the nipple formed from skin of the latissimus dorsi flap. Due to the excellent blood supply with the latissimus dorsi flap, areolar tissue grafting and the formation of the nipple can take place at this initial stage. Accordingly, an immediate, complete, one-stage breast reconstruction is performed.

The use of a latissimus dorsi flap creates a large submuscular compartment. Even though the latissimus dorsi procedure creates a large submuscular pocket, the post-procedure unoccupied volume within the breast is small. Thus, with latissimus dorsi flap procedures there is no need to use a breast expander to stretch remaining breast tissue so that an appropriately sized implant can be accommodated. A permanent prosthetic implant can be inserted at the initial stage, and a reconstructed breast having a volume corresponding to the contralateral breast results. No breast expander prosthesis is required which would necessitate subsequent medical intervention to appropriately adjust. Thus, the size of the submuscular compartment along with the volume of the muscle in the reconstructed breast permits use of a permanent prosthetic implant.

The present procedure can be used for a variety of breast shapes and sizes. In patients having smaller breasts, the need for an implant may be eliminated altogether. For women with large or ptotic breasts, a permanent implant will generally be indicated, in order to match the size of the contralateral breast. For women with large or extremely ptotic breasts, a breast reduction or nipple-areolar complex repositioning may be used concurrently with the procedure of the present invention.

Thus, it is an advantage of the procedure that a single-stage aesthetically pleasing breast reconstruction is possible. By use of this procedure, the typical transverse mastectomy scar and the characteristic mastectomy deformity are both avoided. Furthermore, the procedure can also be used bilaterally.

It is also an advantage that a permanent breast implant can be used. Use of a permanent implant overcomes the necessity for any procedures to adjust breast volume with a breast expander, and then to subsequently replace the expander with a permanent implant. As a further advantage, the need for a subsequent repositioning surgery on the contralateral breast is frequently avoided, since the skin envelope on the mastectomy site is completely preserved. Complete preservation of the skin envelope on the mastectomy side, and the fact that the procedure yields a reconstructed breast with a volume comparable to the contralateral breast, frequently overcomes the necessity of repositioning incisions to size-adjust the contralateral breast. Thus, contralateral breast repositioning, with resultant scarring, is eliminated. Accordingly, the procedure is significantly less costly than prior procedures, since a single-stage breast reconstruction is available, and the need to size-adjust the contralateral breast is generally overcome. Furthermore, the invention concomitantly produces an aesthetically improved result.

DETAILED DESCRIPTION OF THE PREFERRED EMBODIMENTS

For the first time in the art, a latissimus dorsi flap breast reconstruction is combined with a modified radical circumareolar mastectomy. A circumareolar mastectomy is a mastectomy performed through a substantially circumareolar excision. As used herein, a "substantially circumareolar incision" comprises an incision that circumscribes at the perimeter of the nipple-areolar complex; in instances where a breast reduction and/or a nipple-areolar repositioning is to be performed, an incision that circumscribes at the perimeter of the nipple-areolar complex and includes additional breast skin; and, an incision that approximates the areolar perimeter yet is within the area of the areola. The procedure of the present invention is a method of total and immediate breast reconstruction that eliminates the transverse mastectomy scar, and is performed in a single stage. Advantageously, a reconstructed breast produced in accordance with the present invention has better contour and projection than reconstructed breasts resulting from prior procedures.

Preferably, a latissimus dorsi muscular flap having a cutaneous peg of dermal, and most preferably dermal and epidermal tissue is used. However, a muscular flap that does not have a cutaneous peg may also be used in accordance with the invention. As used herein, a cutaneous peg comprises dermal tissue, and typically comprises epidermal and dermal tissue. Preferably, the peg has an superficial epidermal area that corresponds to the two-dimensional area of the incision opening, and a three-dimensional frusto-conical shape that corresponds to the shape of the excised nipple-areolar complex. Thus, a muscular flap with the preferred cutaneous peg serves as an elevated platform from which a nipple-areolar complex can be reconstructed.

Since the procedure provides a method for an immediate and total breast reconstruction, the patient does not experience a mastectomy deformity and accompanying emotional trauma. Since the mastectomy is performed through a circumareolar incision, there is no transverse mastectomy scar, the scar is camouflaged around the perimeter of the reconstructed nipple-areolar complex. In contrast to former latissimus dorsi flap procedures, a smaller donor site scar also results in accordance with the present procedure. Advantageously, due to the improved circulation of a latissimus dorsi flap versus other flaps, the patient's own areola can be harvested and incorporated within the immediate nipple-areolar reconstruction. The reconstruction technique of the present invention is appropriate for the complete range of breast sizes, and can be performed bilaterally.

It is preferred that the surgeon limit any biopsy and subsequent mastectomy skin excision to the region of the nipple-areolar complex. Direct tumor involvement of the breast skin, although infrequent, will typically preclude the applicability of this procedure. When the skin excision in a mastectomy is limited to the region of the nipple-areolar complex the skin envelope of the breast is completely preserved.

The initial breast biopsy site should be within the region of the areola, so that the preferred embodiments of this surgery remain available to patients. The biopsy skin incision is generally removed at the time of the mastectomy, therefore, biopsy incisions outside the region of the areola will often require too great a skin excision. Commonly, for biopsies outside the region of the nipple-areolar complex, a skin island larger than the circular peg which corresponds to the size of the areola would be required. Disadvantageously, the mastectomy scar would no longer be camouflaged at the border of the areola and the reconstructed breast would not have normal contour.

Preferably, the circumareolar incision closely corresponds to the perimeter of the areola, and is at or within the margin of the areola. Although less ideal since they create scarring that does not correspond to a natural tissue plane, radial skin incisions at the border of the areola can be accommodated in accordance with the present procedure.

Mastectomy excisions through a substantially circumareolar incision that is larger than the areolar perimeter can be performed in accordance with the invention, particularly for patients for whom a breast reduction and/or nipple-areolar repositioning is indicated. In the case of a patient requiring a breast reduction and/or nipple-areolar repositioning, a "substantially circumareolar incision" is one that corresponds to the perimeter of the areola and comprises an incision that corresponds to a standard pattern reduction or repositioning incision. Accordingly, for the patient undergoing a nipple-areolar repositioning and/or a breast reduction, a cutaneous peg is still used that has a superficial surface that corresponds in size to the two-dimensional area of the excised nipple-areolar complex, and the resulting scar is substantially along the border of the reconstructed areola. In general, however, if a skin flap is used that extends beyond the perimeter of the nipple-areolar complex, the resulting mastectomy scar is more readily apparent; the contour and projection of the reconstructed breast will be flatter and less natural. Thus, in accordance with the invention, a mastectomy with a substantially circumareolar incision results in a reconstructed breast that has a greatly improved aesthetic result.

Alternatively, yet also in accordance with the present invention, a variable amount of areola may be left with the breast skin. In such a situation, for example, the cutaneous peg could then be used to reconstruct only the excised nipple.

Radiation therapy is known to those skilled in the art to be less distorting if performed after a breast reconstruction. Thus, patients necessitating postoperative radiation therapy can be candidates for the procedure of the invention. The procedure would not alter the patient's post-operative prognosis. Size or stage of the breast cancer will not limit applicability of the procedure, so long as there is not invasion of the skin or of the thoracodorsal bundle. If invasion of the skin or the thoracodorsal bundle has occurred, a standard modified radical mastectomy with dissection of lymph nodes would generally be performed.

Figure 2:
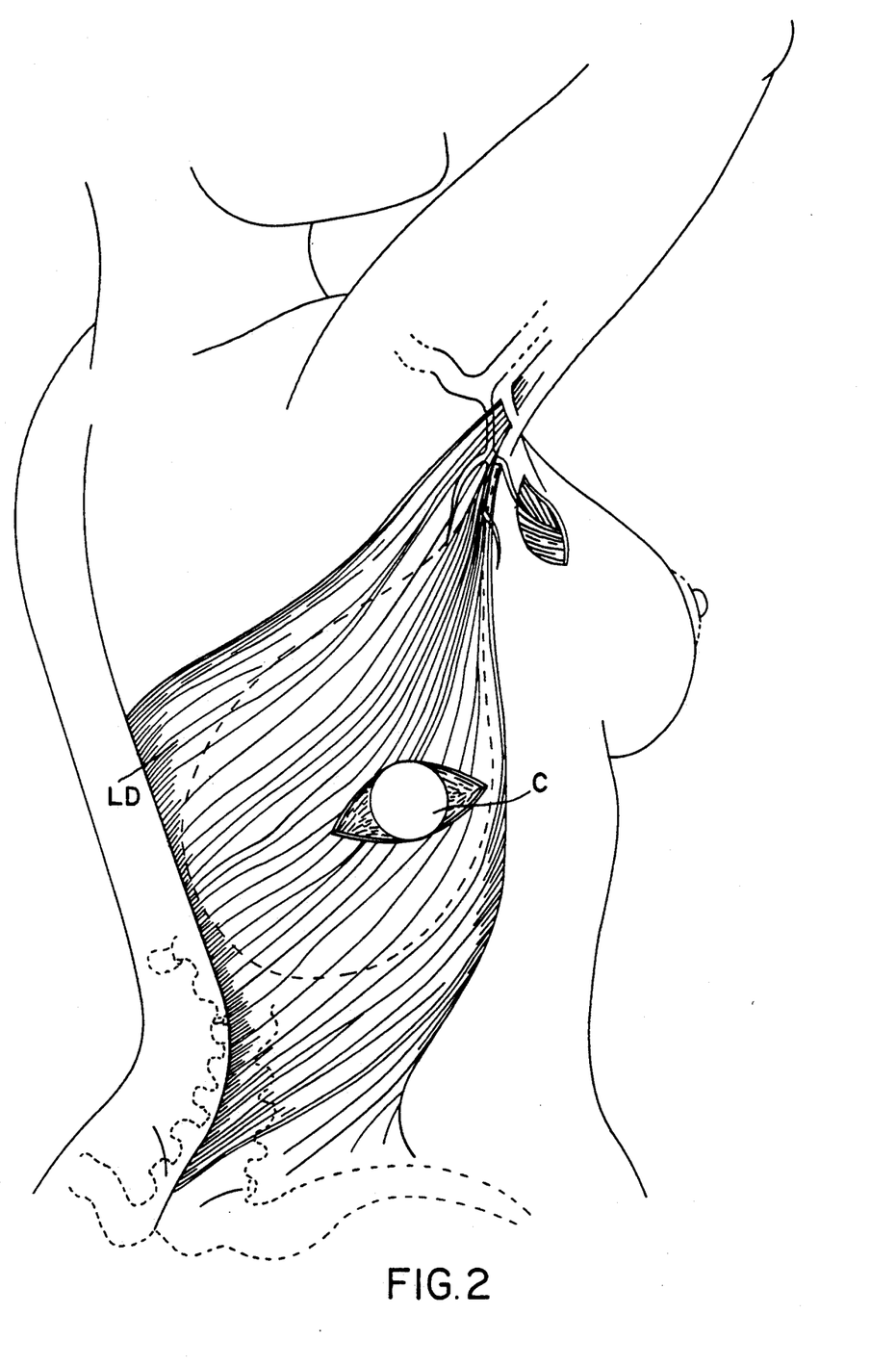
FIG. 2 illustrates a latissimus dorsi muscle, the outline of the latissimus dorsi flap and the cutaneous peg of the flap.

The preferred surgery of the present invention applies techniques known in use of latissimus dorsi myocutaneous flap reconstructive procedures. However, unlike prior procedures, a specially designed cutaneous island (peg) on a latissimus dorsi flap will be raised. FIG. 2 illustrates the latissimus dorsi muscle LD; the cutaneous peg C; and the shape of the flap, which is depicted in broken outline.

Figure 4:
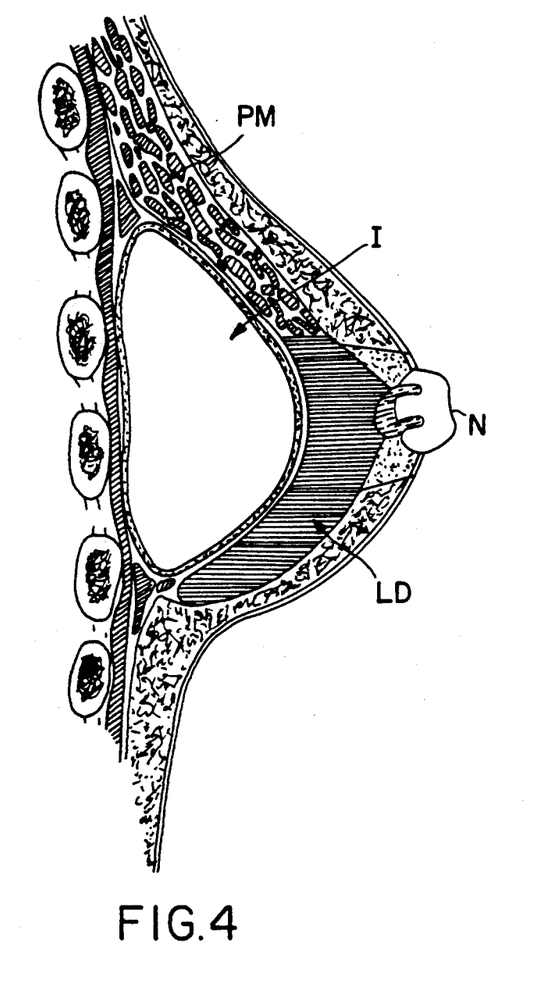
FIG. 4 illustrates a superior-inferior crosssection of a reconstructed breast.

The myocutaneous unit in a latissimus dorsi flap procedure differs substantially from a myocutaneous unit in a TRAM flap procedure. In the TRAM flap procedure, the majority of the myocutaneous unit is composed of subcutaneous adipose tissue; this adipose tissue provides most of the volume for the reconstructed breast. The muscular component of the TRAM flap serves merely as a vehicle for the vascular conduit to the cutaneous island of the flap. In a TRAM flap reconstruction, the muscular component does not provide a muscular sling that could be used for the creation of a submuscular prosthetic pocket. If prosthetic implants are used with a TRAM flap reconstruction, the implants are generally premuscular, a location that can impair diagnosis of any cancer recurrence. With a latissimus dorsi myocutaneous unit, in contrast, musculature provides a substantial part of the volume of a reconstructed breast. The muscular component of the latissimus dorsi myocutaneous unit LD readily can be used for the creation of a submuscular pocket which can contain an implant I, as illustrated in FIG. 4. Thus, should a cancer recurrence occur, the latissimus dorsi flap together with a prosthetic implant would not unduly impair diagnosis.

The present invention can be performed on both breasts. Thus, if a subsequent breast cancer occurs in the contralateral breast, the same procedure can be performed. Alternatively, if a bilateral breast cancer is present, one or both breasts can be reconstructed with this technique.

A preferred form of the invention will now be described. The patient is initially placed in a lateral decubitus position, so that the breast requiring the mastectomy is raised. The initial incision is made in the axilla; the incision is of sufficient size to perform axially lymph node dissection, and identify the latissimus dorsi and teres major muscles and the thoracodorsal artery and vein. (Bostwick et al.: *Breast Reconstruction After Radical Mastectomy. Plast. Reconstr. Suro.* 61:682, (1978)) The axillary incision can extend along the posterior margin of the axilla. The flap dissection plane must be anterior to the thoracodorsal bundle. (Knowlton E. W.: *"Release of Axillary Scar Contracture with a Latissimus Dorsi Flap," Plast. Reconstr. Surg.* 74:124–126, (1984)) If the dissection plane is not anterior to the vascular bundle, the latissimus dorsi flap will die because it will be deprived of vascular supply. A portion of the insertion of the latissimus dorsi is transected, near the axilla, in order to provide further exposure and to increase the arc of rotation of the flap, as illustrated in FIG. 2. Although the thoracodorsal artery is transferred with the flap, lumbar perforators, for example, supply the remainder of the muscle. Then, a plane of deep dissection subjacent to the latissimus dorsi is carried out; this plane is immediately above the teres major muscle. This dissection is performed superior to the area in which the thoracodorsal artery enters.

The area of cutaneous tissue C that will constitute the peg of the latissimus dorsi flap is marked at the bra line, near the anterior border of the latissimus dorsi muscle, as shown in FIG. 2. By cutaneous it is meant a deepithelialized or a full thickness region. The exterior surface of the cutaneous peg C is substantially circular so as to correspond to the area of the incision opening. Preferably, the tissue of the peg underlying the surface is contoured to make the peg frusto-conical in shape, so that the peg corresponds to the shape and size of the nipple-areolar complex. Such contouring serves to create a donor tissue that more closely corresponds to the normal contour of the nipple-areolar complex than prior techniques. Approximately triangular shaped areas of skin on both sides of the skin peg on the latissimus dorsi flap are deepithelialized or excised so that the donor site can be closed as a linear incision. Additionally, by removing the surrounding subcutaneous tissue from the peg, a more natural projection of the peg in its eventual location within the circumareolar incision will result. Preferably, by removing subcutaneous tissue from the peg, frusto-conical peg shape results. Thus, three dimensional congruence between the mastectomy defect and the peg of the latissimus dorsi flap are important for the most advantageous outcome of this procedure.

Figure 3:
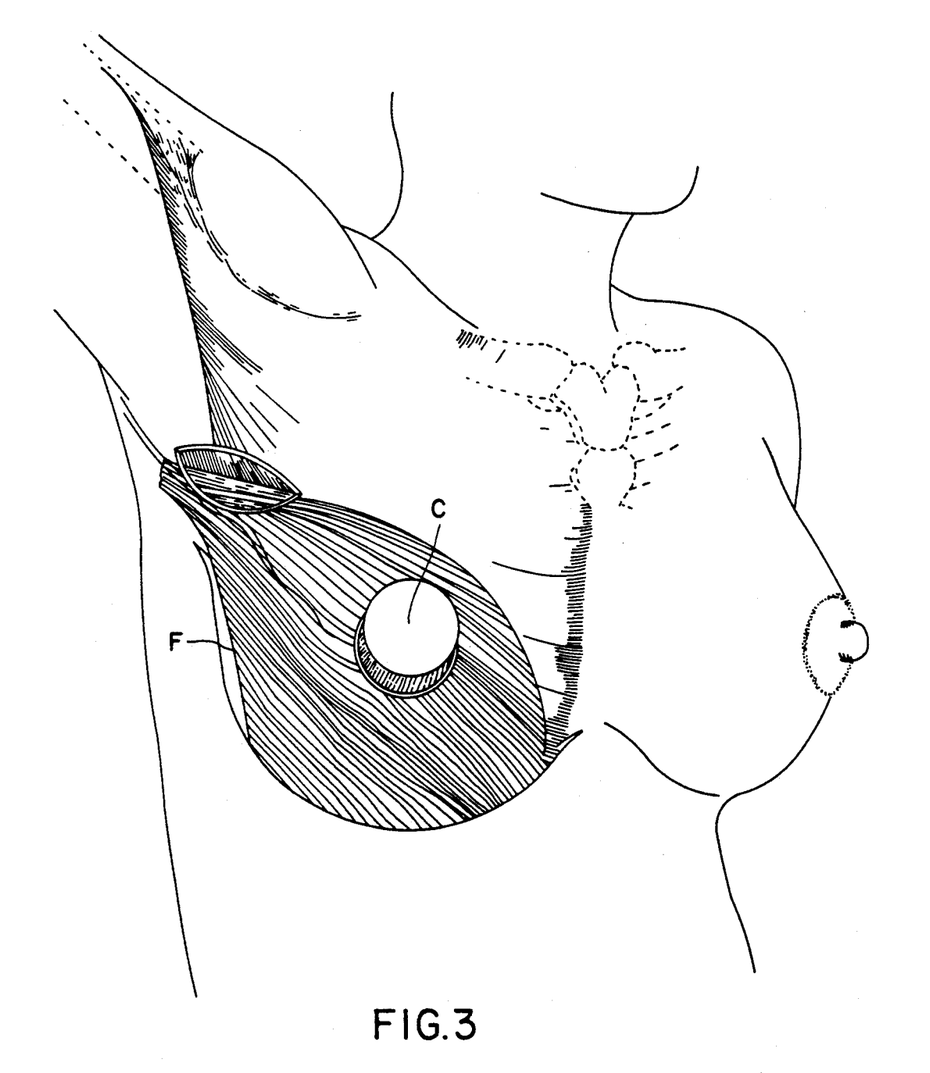
FIG. 3 illustrates the latissimus dorsi flap moved into the mastectomy defect, with the peg protruding through the periareolar incision.

An inferior back incision is then made. The inferior back incision is transverse and on the ipsilateral side as the mastectomy. A portion of the latissimus dorsi should be included inferior and posterior to the region of the peg. As illustrated in FIG. 3, the portion of the muscle flap F that is inferior and posterior to the peg should be sized so that it will lay loosely between the circumareolar incision and the inframammary skin fold. Thus, the flap F corresponds to a perimeter of the intact breast skin envelope which is at least partially defined by the inframammary skin fold. The size of the flap also allows complete coverage of the implant in its submuscular compartment. The inferior incision (flap donor site incision) may be begun above the peg of the flap in the superficial plane. It is advantageous to include some subcutaneous tissue on the flap for added tissue volume within the breast, and as a soft tissue buffer to lessen the effect of muscle contraction or tightening on the overlaying breast skin. It is a particular advantage that the contour irregularities of a saline implant are greatly reduced with the present invention.

Proceeding from the inferior incision, the plane of deep dissection subjacent the latissimus dorsi should be between the serratus anterior and latissimus dorsi muscles, the dissection begun along the anterior border. (Schneider et al.: *Latissimus Dorsi Myocutaneous Flap for Breast Reconstruction.*, Br. J. Plast. Surg. 30:277, (1977)) The serratus anterior is immediately subjacent to the latissimus dorsi. It is very easy to pick up the serratus anterior along with the latissimus dorsi during dissection. The adherent serratus anterior is sharply dissected from the underside of the latissimus dorsi muscle. If the serratus anterior has inadvertently been raised along with the latissimus dorsi, the serratus should simply be resutured to the tissues covering the rib cage. The surgeon can know that he or she is working in the appropriate plane between the serratus anterior and the latissimus dorsi if the plane of dissection carries over the scapula. If the plane of dissection is internal to the scapula, the surgeon has gone one layer too deep and the serratus anterior is being raised.

The inferior border of the latissimus dorsi flap is then incised. Elevation of the flap is then accomplished by connecting the planes of deep dissection extending from the superior and inferior back incisions.

When properly dissected, the only structure holding the flap is the vascular connection. To prevent torsion of the vascular connection, the branch of the thoracodorsal artery leading to the serratus anterior muscle may be transected. When moving the flap the vascular connection is easily rotated, resulting in vascular compromise. Care should be taken to avoid torsion of the vessel.

The flap is moved to a subcutaneous axillary location. The back incisions are then closed and a drain is placed at the flap donor site incision. The drain should be in place approximately one week, since a seroma may readily form if the drain is removed too quickly. However, autologous fibrin sealant is known to reduce the incidence of seroma formation at the flap donor site.

The patient is then placed in a supine position. A mastectomy is then performed through a circumareolar incision, such as by the procedure of Grossman et al.: *An Alternative Technique for Modified Radical Mastectomy with Immediate Reconstruction.* Contemp. Suro. 38(6):20-24, (1991). The surgeon generally proceeds as would be done with a large incision mastectomy. However, cautery is avoided. It is believed that subcutaneous tissue dissection without cautery results in less damage to the subdermal plexus. Much of the bleeding which is encountered is subcutaneous bleeding, which can be controlled merely by packing. During dissection of the breast tissue, care is taken not to damage the flap's vascular pedicle which is located in the region of the axilla.

Figure 7:
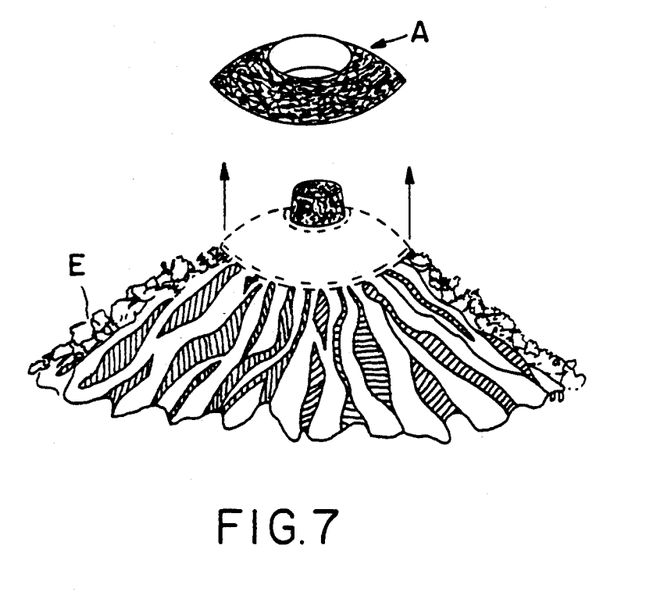
FIG. 7 illustrates harvesting of the areola from excised breast tissue.

The areola A may then be harvested from excised breast tissue E, as illustrated in FIG. 7. Areolar harvesting may be performed if there is no invasion of the nipple-areolar tissues. The areola is harvested as a full thickness skin graft. Advantageously, the harvested areola functions as the most accurate areolar donor for reconstruction of the patient's nipple-areolar complex.

A subcutaneous pathway is then opened between the location of the flap in the axilla and the mastectomy defect. This pathway is sufficiently large so that postoperative edema does not occlude the vascular flow through the pedicle supplying the latissimus dorsi flap. Thereafter, the flap is delivered from the axilla into the region of the mastectomy defect. At this stage, care is again taken to verify that the vascular pedicle to the flap has not been compromised. The axillary incision can be reopened if assistance is needed in advancing the flap towards the mastectomy defect.

The inferior border of the latissimus dorsi flap is then sutured, or otherwise attached, to the inframammary skin fold. Thereby, a submuscular pocket is created. If there is any tension on the flap as it is being sutured to the inframammary fold, the insertion of the latissimus dorsi flap has not been sufficiently released. The axillary incision can then be reopened to more completely release the insertion.

A subpectoral portion of the submuscular pocket is created by releasing the fibers of origin of the pectoralis major muscle up to the mid-sternum. If malignancy has invaded the lower border of the pectoralis major, excision of this tissue will not preclude use of the invention. Previously, if the breast cancer required resection of the fascia and a portion of the pectoralis major, this would limit the ability to insert a breast expander or permanent implant in a subpectoral pocket. With the additional inlay of latissimus dorsi this is no longer a limitation.

The present invention can still be used because of the added volume provided by the latissimus dorsi muscle.

The breast implant I is then placed in the submuscular pocket, as illustrated in FIG. 4. The size of the implant will, as is known to those in the art, vary greatly. For women with small breasts, an implant may not be necessary. (McCraw & Papp: *Fleur-de-Lis Breast Reconstruction*. In: *Hartramof's Breast Reconstruction with Living Tissue*, pp 211-248. (Hampton Press, Norfolk, VA, 1991)) For women in whom an implant is not needed, it will not have been necessary to dissect a subpectoral pocket. When selecting an implant size, the fact that the muscular flap will undergo atrophy must be taken into account. To best establish that the appropriate size implant has been selected, the patient should be moved into a sitting-up position.

A drain is then inserted into the axilla, through a separate stab incision. The implant is then secured in place by suturing the superior border of the latissimus dorsi flap to the inferior border of the pectoralis major. Due to the presence of the latissimus dorsi flap and the submuscular prosthetic pocket that collectively approximate the volume of the excised tissue, an interim breast expander is not necessary.

Accordingly, when an implant is placed in the submuscular compartment, the implant along with the flap volume approximates that of the excised tissue. A submuscular pocket, beneath the pectoralis major muscle PM and the latissimus dorsi flap LD, is shown containing an implant I, in FIG. 4. Thus, a significant advantage of the invention is that the combination of the pectoralis major and the latissimus dorsi flap having a cutaneous peg corresponding to a circumareolar incision produces a reconstructed breast that closely approximates the volume of the contralateral breast, as well as the shape and contour of the normal breast skin envelope. Advantageously, this breast skin envelope is preserved as a result of the circumareolar mastectomy.

Figure 5:
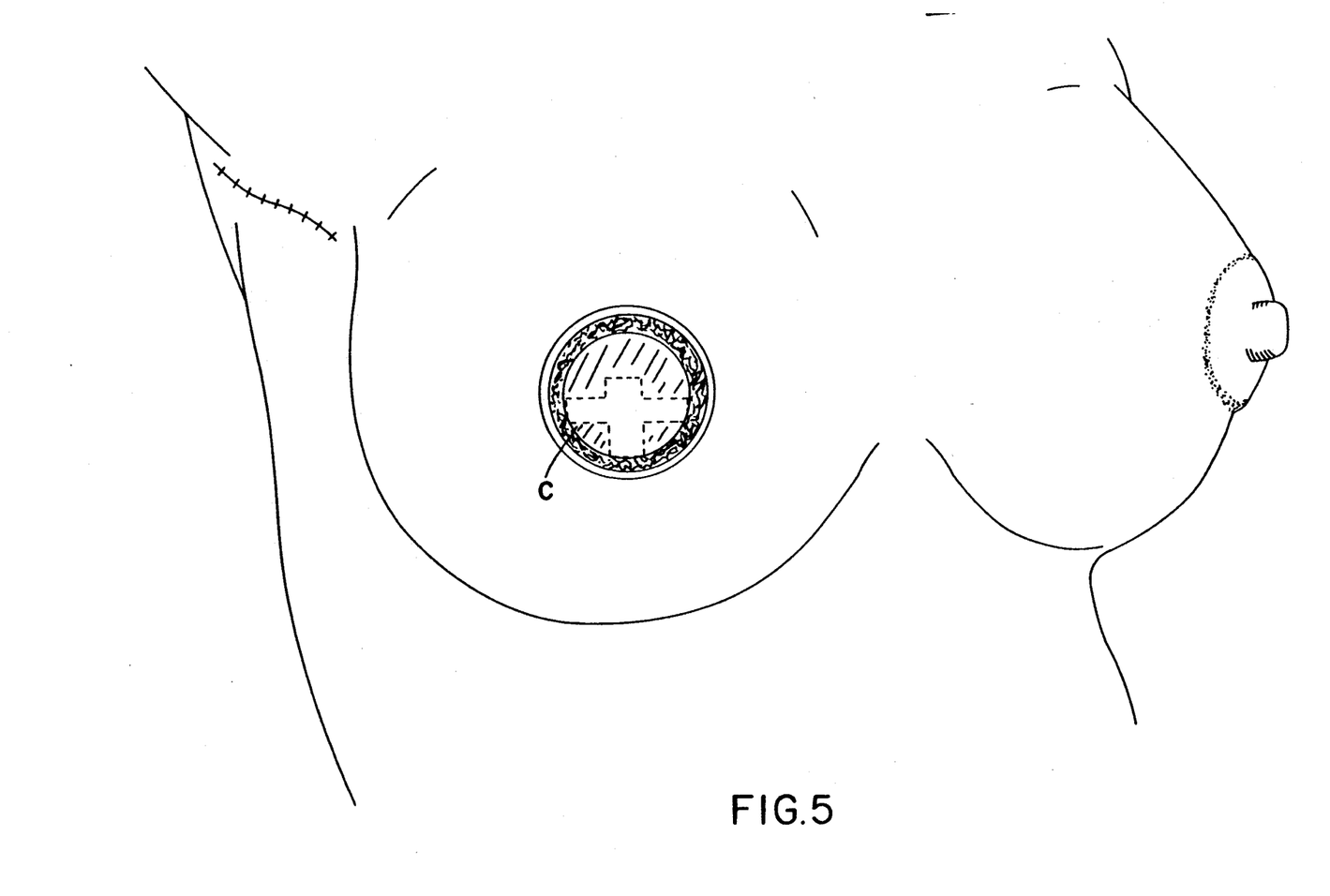
FIG. 5 illustrates markings on the skin peg that will constitute the quadraped nipple.
Figure 6:
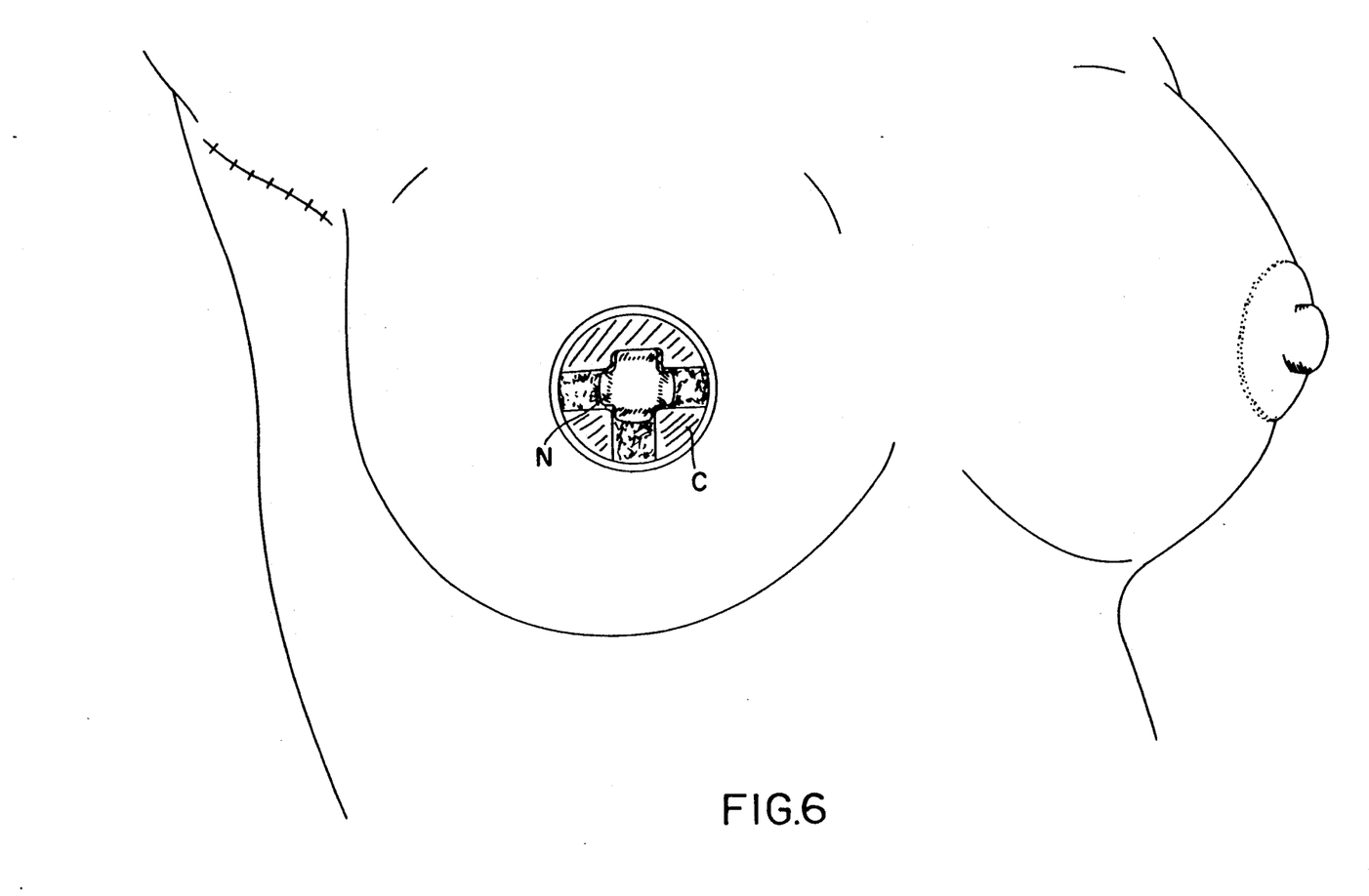
FIG. 6 illustrates the elevated quadraped nipple, after the peg has been sutured to the margin of the incision.

The cutaneous peg is then used to close the substantially circular defect of the excised nipple-areolar complex. Advantageously, due to the excellent circulation of the latissimus dorsi flap, the nipple-areolar complex can be reconstructed immediately by creating a nipple mound from the skin peg (FIGS. 5 and 6). However, if there is any question that there may not be sufficient vascular flow to the latissimus dorsi flap, the procedure can be terminated at this stage. If there is no vascular compromise to the flap, reconstruction of the nipple-areolar complex can take place. However, if nipple reconstruction does not take place immediately, the surgery is terminated after the margin of the latissimus dorsi skin peg is sutured, or otherwise attached, to the margin of the breast that circumscribed the excised nipple-areolar complex.

Preferably, the nipple N is reconstructed from a superiorly pedicled quadraped flap, as illustrated in FIGS. 5 and 6. The flaps are marked (as illustrated in FIG. 5), and the quadrants between the flaps are then deepithelialized (as illustrated in FIG. 6). Because the nipple N will rise superiorly as the flaps are sutured, the initial location is somewhat inferior to the preferred eventual location. Then, the three inferior flaps are raised by undermining. The undermining of the three flaps extends to the area subjacent to the reconstructed nipple. The superior flap will serve as the vascular pedicle and will not be raised, as illustrated in FIG. 5. The width of the flaps and the amount of subcutaneous tissue that is to be included when raising the flaps varies between patients, as will be known to skilled artisans. It is generally preferable to overestimate the amount of tissue that is needed, to account for postoperative atrophy. The flaps are then sutured so that a nipple is raised, the excess skin of the three inferior flaps is then removed, and the superior flap is deepithelialized. The superior flap is not removed full thickness, since the vascular supply to the reconstructed nipple would be removed as well.

Preferably, an areolar graft is then sutured in place. Most preferably, this tissue is harvested from the patient's own excised nipple-areolar complex. Rather than discarding the areola A, as is commonly done, the areola can be defatted (as illustrated in FIG. 7), and placed as a full-thickness skin graft to the deepithelialized peg (as illustrated in FIG. 6). The highly vascularized nature of the latissimus dorsi flap allows grafting to occur contemporaneously. Alternate skin graft donor sites for the areola are known to those skilled in the art. For example, the areola can be reconstructed with either full thickness or split thickness skin grafts from the thigh, groin, labia, post-auricular skin, and any other readily available skin graft donor sites. Approximately six to eight weeks post-operatively, the patient can undergo tattooing or micropigmentation of the nipple.

Alternatively, nipple flap elevation may occur without additional skin grafting. If the nipple is raised from the area of the latissimus dorsi peg without additional skin grafting, subsequent tattooing will occur over the entire nipple-areolar complex, rather than just to the nipple area.

Alternate methods of nipple-areolar reconstruction are known to those skilled in the art. Such methods include nipple mound reconstruction with quadraped, triped or biped pedicled flaps; or with subcutaneously pedicled quadraped or triped flaps. Nipple projection could also be obtained through the use of ear cartilage, or the use of a subcutaneously implanted nipple prosthesis.

A preferred embodiment of the latissimus dorsi peg flap procedure comprises a peg that serves as an elevated platform upon which to reconstruct the nipple-areolar complex. Accordingly, a reconstructed breast results that more accurately replicates the three dimensional projection of a normal nipple-areolar complex. Preferably, the projection of the constructed nipple-areolar complex corresponds to the natural nipple-areolar complex due to the depth and shape of the circular peg of the flap. Since the dimensions of the peg are designed to match the excised nipple-areolar complex, beveling of the subcutaneous tissue adjacent to the cutaneous peg can help to further simulate the normal projection of the nipple-areolar complex. This breast contour and projection has not been available with former procedures.

As is known to those skilled in the art, antibiotics should be used throughout the procedure. Typically 1 gm of Vancomycin, currently the most effective antibiotic for suppressing *Staphyloccus epidermis* contamination from the breast tissue, is administered via IV piggyback.

For women with large or ptotic breasts, a breast reduction and/or nipple-areolar repositioning may be used in combination with the latissimus dorsi peg breast reconstruction of the present invention. A breast reduction and/or nipple-areolar repositioning can be performed according to procedures known to those of skill in the art. For example, a breast reconstruction can be performed by a Wise pattern (keyhole) skin reduction.

In such cases, the contralateral breast would also undergo a similar Wise pattern breast reduction. An appropriately sized permanent implant is used to substitute for the missing breast tissue on the mastectomy side; the reconstructed breast corresponds to the volume of the size-reduced contralateral breast. Thus, both breasts would have typical breast reduction/nipple repositioning incisions. The nipple-areolar complex at the mastectomy site is reconstructed with the circular peg of the latissimus dorsi flap, while on the contralateral breast the nipple-areolar complex is transposed to the same level as the peg flap of the mastectomy site. In contrast, women with small or moderately ptotic breasts would not require correction of the contralateral side. No correction is required for these women since the skin on the mastectomy side remains completely intact and the volume of the breast reconstructed with the latissimus dorsi flap corresponds to the volume of the contralateral breast.

EXAMPLES

EXAMPLE 1

A 57-year-old Caucasian female underwent a left modified radical mastectomy with axillary lymph node dissection. The skin excision was limited to a circumareolar resection. An immediate breast reconstruction was performed using a latissimus dorsi flap having a cutaneous peg. A permanent textured silicone implant was placed into the combined submuscular compartment of the pectoralis major and latissimus dorsi. The nipple-areolar complex was reconstructed eight weeks later. The contralateral nipple-areolar complex was raised with excision of a superior periareolar ellipse of skin.

EXAMPLE 2

A 44-year-old Caucasian female, who had diffuse carcinoma in situ of the right breast, underwent a right modified radical mastectomy with axillary lymph node dissection. The skin excision was limited to a circumareolar resection. An immediate breast reconstruction was performed with a latissimus dorsi flap having a cutaneous peg. A permanent textured saline implant was placed into the combined submuscular compartment. The nipple-areolar complex was reconstructed immediately using a quadraped flap for the nipple. The ipsilateral areola was harvested, and attached as a full-thickness skin graft to the recipient areolar site of the peg flap.

EXAMPLE 3

A 46-year-old Caucasian female with moderately ptotic breasts having large areolae underwent a right modified radical mastectomy with axillary lymph node dissection. A permanent silicone implant was inserted into the combined submuscular compartment of the pectoralis major and latissimus dorsi.

Due to the increased width of the nipple-areolar complex and ptosis of the right breast, the circumareolar skin excision for the mastectomy comprised a modified Wise key-hole-shaped resection. A modified Wise keyhole-shaped resection was also performed on the contralateral breast. A peg from the right latissimus dorsi replaced the excised nipple-areolar complex, thereby matching the area of the contralateral nipple-areolar complex. Both the ipsilateral and the contralateral nipple-areolar complexes were elevated to comparable and slightly higher positions.

The right nipple-areolar complex was constructed immediately using a quadraped flap for the nipple. The ipsilateral areola was harvested, and attached as a full-thickness skin graft to the recipient areolar site of the peg flap.

CONCLUSION

Advantages of the procedure of the present invention include camouflaging of the scar around the perimeter of the nipple, and the improved projection of the reconstructed nipple-areolar complex. Further, with the procedure there is essentially no muscular function loss consequent to the movement of the latissimus dorsi flap. The teres major will compensate for the loss of the latissimus dorsi muscle.

The myocutaneous peg flap procedure is performed as a single-stage, total and immediate breast reconstruction. In general, the procedure eliminates the costs of multi-stage reconstructions, and the costs of procedures to size-adjust the contralateral breast. Accordingly, there is a significant reduction in health care costs in relationship to a multi-staged breast reconstruction or to a TRAM flap procedure.

Although the present invention has been particularly described with regard to open surgical techniques, other surgical techniques are within the scope of the invention. For example, endoscopic dissection of a myocutaneous peg flap and the mastectomy site may be performed. Although certain embodiments of the procedure have been set forth, these embodiments are not to be construed as limiting the invention. Other medical techniques and sequences of performing the steps of the procedure can be utilized, as will be known to those of skill in the art. The procedure of the present invention is fully disclosed herein. Procedures that correspond to the present disclosure are addressed in the article by Knowlton, "Total Immediate Breast Reconstruction with 'Peg' Latissimus Dorsi Flap," *Contemporary Surgery* 41:15–19 (September 1992); and in the videotape "The Peg Latissimus Dorsi Flap Procedure" (Medical Media Productions, Sausalito, CA (1992)), both of which are incorporated by reference herein. The Knowlton *Contemporary Surgery* 41:15 (September 1992) article, and the "The Peg Latissimus Dorsi Flap Procedure" videotape are directed to skilled artisans, and address preferred embodiments and the best mode for performing the procedure of the present invention. It is understood that the scope of the invention is limited only by the claims.

What is claimed is:

1. A surgical method, comprising the contemporaneous steps of:
    performing a mastectomy on a breast through a substantially circumareolar incision, thereby creating an incision opening; and
    reconstructing the breast with a latissimus dorsi flap.
2. The method of claim 1, wherein the latissimus dorsi flap is a myocutaneous flap.
3. The method of claim 2, wherein the latissimus dorsi flap has a cutaneous peg corresponding in size to the incision opening.
4. The method of claim 3, wherein the reconstruction comprises closing the incision with the peg.
5. The method of claim 3, wherein the peg is substantially frusto-conical in shape.

6. A method for contemporaneous post-mastectomy breast reconstruction, the mastectomy resulting in a mastectomy defect and the mastectomy performed through a substantially circumareolar incision opening so that an intact skin envelope of the breast is preserved, comprising steps of:

creating a lattissimus dorsi flap;

moving the flap to the mastectomy defect;

attaching the flap within the mastectomy defect; and closing the incision opening with use of the cutaneous peg of the flap.

7. The method of claim 6, wherein the attaching step creates a submuscular pocket beneath the latissimus dorsi flap, prior to the closing step.

8. The method of claim 7, further comprising a step of placing an implant in the submuscular pocket, prior to the closing step.

9. The method of claim 6, further comprising a step of reconstructing a nipple-areolar complex, after the closing step.

10. The method of claim 9, wherein the reconstructing step comprises:

harvesting areolar tissue from excised breast tissue; and utilizing the harvested tissue to reconstruct the nipple-areolar complex.

11. The method of claim 6, further comprising a step of performing a breast reduction procedure.

12. The method of claim 6, further comprising a step of performing a nipple-areolar repositioning procedure.

13. The method of claim 6, wherein the creating step creates a latissimus dorsi flap having a perimeter that substantially corresponds to a perimeter of the skin envelope.

14. The method of claim 13, wherein the breast comprises an inframammary fold, and wherein the perimeter of the skin envelope comprises the inframammary fold.

15. The method of claim 6, wherein the peg is substantially frusto-conical in shape.

16. A method for contemporaneous postmastectomy breast reconstruction, the mastectomy resulting in a mastectomy defect and the mastectomy performed through a substantially circumareolar incision opening so that an intact skin envelope of the breast is preserved and the mastectomy results in the substantially excision of a nipple-areolar complex having a three-dimensional size and shape, the method comprising steps of:

marking a cutaneous peg over a latissimus dorsi muscle ipsilateral to the mastectomy, the peg comprising a cutaneous portion;

creating a latissimus dorsi flap having the cutaneous peg and a functioning vascular connection;

establishing an internal pathway between the initial site of the flap and the mastectomy defect, the pathway being sized so that the flap can be moved through the pathway and so that the functioning vascular connection to the flap is preserved;

moving the flap through the pathway into the mastectomy defect;

attaching the flap within the mastectomy defect; and closing the incision with use of the cutaneous peg of the flap.

17. The method of claim 16, wherein the creating step creates a flap extending at least from the vascular connection to inferior to the skin peg.

18. The method of claim 16, wherein the creating step creates a latissimus dorsi flap having a perimeter that substantially corresponds to a perimeter of the skin envelope.

19. The method of claim 18, wherein the breast comprises an inframammary fold, and wherein the perimeter of the skin envelope substantially comprises the inframammary fold.

20. The method of claim 16, wherein the creating step creates a peg that corresponds to the threedimensional size and shape of the excised nipple-areolar complex.

21. The method of claim 20, wherein the peg is substantially frusto-conical.

22. The method of claim 16, further comprising a step of dissecting a submuscular pocket, subjacent to an ipsilateral pectoralis major muscle.

23. The method of claim 22, wherein the attaching step comprises attaching the latissimus dorsi flap to an inferior border of the mastectomy defect so that the submuscular pocket is expanded.

24. The method of claim 23, wherein the breast comprises an inframammary fold, and wherein the inferior border of the submuscular pocket is the inframammary fold.

25. The method of claim 23, further comprising a step of placing an implant into the submuscular pocket.

26. The method of claim 25, further comprising a step of securing the implant in the submuscular pocket by attaching an inferior border of an ipsilateral pectoralis major muscle to a superior border of the latissimus dorsi flap.

27. The method of claim 16, further comprising a step of reconstructing a nipple-areolar complex.

28. The method of claim 27, wherein the reconstructing step comprises:

harvesting areolar tissue from ipsilateral breast tissue; and utilizing the harvested tissue to reconstruct the nipple-areolar complex.

29. The method of claim 27, wherein a nipple of the nipple-areolar complex is reconstructed from a superiorly pedicled quadraped flap.

30. The method of claim 16, further comprising a step of performing a breast reduction.

31. The method of claim 30, wherein the breast reduction is a Wise pattern skin reduction.

* * * * *